United States Patent [19]

Hill et al.

[11] Patent Number: 5,053,532

[45] Date of Patent: * Oct. 1, 1991

[54] ONE-POT PROCESS FOR THE PREPARATION OF α-L-ASPARTYL-L-PHENYLALANINE METHYL ESTER HYDROCHLORIDE

[75] Inventors: John B. Hill, Woodstock; Yefim Gelman, Arlington Heights; Hugh L. Dryden, Jr., Deerfield; Robert Erickson, Des Plaines; Kuang Hsu, Skokie; Mark R. Johnson, Roselle, all of Ill.

[73] Assignee: The Nutra Sweet Company, Deerfield, Ill.

[ * ] Notice: The portion of the term of this patent subsequent to Aug. 7, 2007 has been disclaimed.

[21] Appl. No.: 547,429

[22] Filed: Jul. 3, 1990

Related U.S. Application Data

[63] Continuation of Ser. No. 156,267, Feb. 12, 1988, abandoned.

[51] Int. Cl.$^5$ .............................................. C07C 229/00
[52] U.S. Cl. ...................................... 562/450; 560/41
[58] Field of Search ........................... 562/450; 560/41

[56] References Cited

U.S. PATENT DOCUMENTS

| | | | |
|---|---|---|---|
| 4,745,210 | 5/1988 | Mita et al. | 560/41 |
| 4,760,164 | 7/1988 | Park et al. | 560/41 |
| 4,810,816 | 3/1989 | Tsuji et al. | 560/41 |
| 4,820,861 | 4/1989 | Yukawa et al. | 560/41 |
| 4,946,988 | 8/1990 | Hill et al. | 562/450 |

*Primary Examiner*—Bruce Gray
*Attorney, Agent, or Firm*—Jeffrey M. Hoster; John M. Sanders

[57] ABSTRACT

A one-pot process for the preparation of α-L-aspartyl-L-phenylalanine methyl ester hydrochloride is disclosed (α-APM(HCl)). α-APM(HCl) is an intermediate in the preparation of aspartame.

6 Claims, No Drawings

ONE-POT PROCESS FOR THE PREPARATION OF α-L-ASPARTYL-L-PHENYLALANINE METHYL ESTER HYDROCHLORIDE

This is a continuation of co-pending U.S. application Ser. No. 156,267, filed Feb. 12, 1988, now abandoned.

Background of the Invention

The present invention relates to a one-pot method for the preparation of alpha(α)-L-aspartyl-L-phenylalanine methyl ester hydrochloride (α-APM(HCl)) which is used to prepare α-L-aspartyl-L-phenylalanine methyl ester (α-APM), a sweetening agent which is approximately 200 times sweeter than sucrose. The potency of this compound, a dipeptide, enables one to sweeten foods and beverages using a far lesser amount than one could with sugar. Consequently, it has enabled millions of consumers to reduce their caloric intake while not having to give up the sweet things in life. It also lacks the unpleasant aftertaste associated with other sweeteners such as saccharin and cyclamate. Additionally, the present invention relates to a method increasing the α/β ratio of APM (HCl) and methods of producing a final reaction mixture of α/β-APM (HCl) having a pourable viscosity.

α-APM is not new and was described in U.S. Pat. No. 3,492,131 to Schlatter in 1970. Numerous other patents involving different methods of manufacture and related compounds have since issued and much literature has been written heralding the effect the dipeptide has had on the low calorie sweetener industry. Up until the present time, however, the methods of preparation have involved costly isolation and recovery processes which consequently must be shouldered by the consumer. The present invention is a method of process whereby a comparable yield of the desired end product is afforded without the need for isolation of intermediates as the prior art heretobefore required.

Alpha-L-aspartyl-L-phenylalanine methyl ester is a dipeptide composed essentially of two amino acids, L-aspartic acid and L-phenylalanine. It has been known for some time that the sweetening property of the dipeptide is dependent upon the stereochemistry of these individual amino acids. Each of these amino acids can exist in either the D or L form, and it has been determined that the L-aspartyl-L-phenylalanine esters are sweet while the corresponding D-D, D-L and L-D isomers are not. Combinations of the isomers which contain the L-L dipeptide; DL-aspartyl-L phenylalanine, L-aspartyl DL-phenylalanine and DL-aspartyl-DL phenylalanine are sweet, but only half as sweet since the racemate contains ½ of the L-L moiety.

The dipeptide is produced through a coupling reaction in which aspartic acid is joined with L-phenylalanine or its methyl ester. This coupling reaction requires an amino protecting group attached to the aspartic acid moiety such as formyl, acetyl, acetoacetyl, benzyl, substituted and unsubstituted carbobenzoxy, t-butoxy carbonyl and the hydrohalide salt. The amino protecting group, often referred to in the art as the N-protecting group, for purposes of this disclosure shall be referred to as N-formyl since the formyl moiety is the blocking agent of the present invention. Formylated aspartic anhydride is a widely used starting material and its process has been described extensively. See U.S. Pat. No. 4,173,562.

The coupling reaction is carried out in a solvent and is a common step in several patented processes for the production of α-L-aspartyl-L-phenylalanine methyl ester (α-APM); see U.S. Pat. No. 3,962,207 to Uchiyama, U.S. Pat. No. 4,173,562 to Bachman and EPO Pat. No. 127,411 to Yaichi et al., all of which are incorporated herein by reference. During the coupling reaction of the two amino acids, two isomers are produced as intermediates and their stereochemistry ultimately determines the sweetness of the particular molecule. The alpha (α) isomer is the desired product in that isolated fractions of pure α-APM possess a sweetness about 200 times that of sugar. The beta (β) isomer fraction, however, has no such sweetness. This invention is directed to improvements in the preparation of α-APM which results in lower costs of production and increased yields of the alpha isomer which is the desired end product.

The α and β isomers of APM are given below:

Alpha Isomer

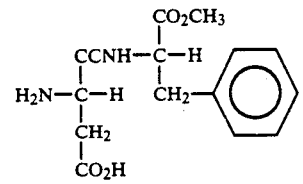

Beta Isomer

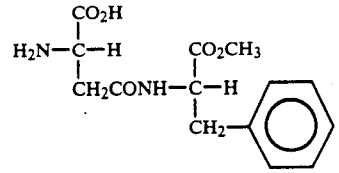

It has been determined that formation of the alpha and beta isomers and their respective ratios from the coupling reaction depends upon what kind of solvent is used to carry out the reaction, the temperature at which the reaction occurs and the quantity of the solvents used. According to U.S. Pat. No. 4,173,562 to Bachman, an alpha/beta isomer ratio of 75:25 is achievable when acetic acid is used as a solvent in the coupling reaction at 50° C. The molar ratio of acetic acid to phenylalanine must be at least 10:1. The alpha/beta isomer ratio drops considerably to 69/31 when the acetic acid to L-phenylalanine molar ratio is reduced to 6:1. The present invention shows that the alpha/beta ratio can be increased to about 80/20 if the acetic acid, used as a solvent in the coupling reaction is partially replaced with an alkyl ester, hindered alcohol or mixture thereof. For purposes of this disclosure, hindered alcohol as it is used herein shall mean a secondary or tertiary alcohol.

A problem that resides with the use of these solvents in this process is that after 0.5–3 hours of reaction time, the reaction mixture solidifies and becomes substantially impossible to agitate or remove from a reactor. A stirrable system is necessary for at least two reasons. On the one hand, stirring insures a mixing of the reactants to achieve a complete reaction. Secondly, solvent must later be removed by distillation.

Another problem that exists in the prior art is that under some techniques, 25% or more of the α-APM is lost because it remains in the original reaction solution. See U.S. Pat. No. 4,173,562. A further problem is that in the '562 patent formyl-L-aspartic anhydride is produced from a reaction mixture of aspartic acid, a large excess of formic acid and acetic anhydride. The excess amount of formic acid must at some point be removed by distillation and separated from acetic acid which adds to the cost of the final product.

U.S. Pat. No. 3,962,207 describes a similar process in which L-aspartic anhydride hydrochloride is coupled with L-phenylalanine methyl ester. A problem that arises in the '207 process is that a large amount of L-phenylalanine methyl ester is required which adds to the cost of the process. Secondly, that results in the formation of significant amounts of tri-peptides which must be removed and thereby necessitate expensive and elaborate separation techniques. This is not required in the present invention.

SUMMARY OF THE INVENTION

The present invention is directed to a process to prepare $\alpha$-APM(HCl). This is performed in a 'one pot' process whereby the reaction by-products produced during formation of the formylated L-aspartic anhydride also serve as the solvent for the coupling reaction in a manner that avoids many of the problems of separation and thereby reduces the cost of preparation. Diluting the coupling reaction with an ester or hindered alcohol improves the yield of $\alpha$-APM(HCl).

Initially, N-formyl-L-aspartic anhydride is prepared by combining aspartic acid with acetic anhydride and formic acid in a reaction process similar to that known in the art. See U.S. Pat. Nos. 3,933,781, 3,962,207 and 4,173,562. The present invention, however, utilizes a minimal amount of formic acid (1.2–1.35 Molar equivalents per mole of aspartic acid) and converts the excess to isopropyl formate by the addition of acetic anhydride and isopropyl alcohol.

The formylated aspartic anhydride can then be coupled in situ by adding L-phenylalanine (L-Phe). An alkyl ester or hindered alcohol is optionally added to the coupling reaction and surprisingly improves the $\alpha/\beta$ ratio. Whereas an ester is normally prepared by reacting an alcohol with an anhydride, it is unexpected that the hindered alcohol does not attack the formyl aspartic anhydride during the course of the reaction. This coupling reaction can be conducted under low or no agitation conditions to keep the viscosity of the reaction mixture low resulting in a pourable final reaction mixture.

The resulting dipeptide is then deformylated with HCl and esterified by adjusting the concentrations of methanol, water and HCl to amounts effective to produce a high yield of $\alpha$-APM(HCl). The $\alpha$-APM(HCl) precipitates from the reaction mixture and is isolated and neutralized with a base to form $\alpha$-APM.

DESCRIPTION OF THE INVENTION

The present invention relates to an improved process for preparing $\alpha$-APM(HCl). The present one-pot process begins by mixing L-aspartic acid with a minimal amount of formic acid (at least 1.2 Molar equivalents based on aspartic acid) and acetic anhydride (at least about 2.0 Molar equivalents based on aspartic acid) in the presence of a catalyst such as magnesium oxide resulting in the formation of N-formyl-L-aspartic anhydride. Suitable catalysts include oxides, hydroxides and salts of metals and are disclosed in U.S. Pat. Nos. 4,508,912 and 4,550,180 which are incorporated herein by reference. This reaction is conducted at temperatures up to about 52° C. The mixture is preferably stirred at about 50° C. for at least about 2.5 hours. Additional acetic anhydride (about 0.2 moles) is added after about 2.5 hours in order to convert any excess, unreacted formic acid to formic-acetic anhydride, i.e., a mixed anhydride. After an additional 2.5 hours, excess isopropyl alcohol (at least about 0.3 molar equivalents based on total formic acid added) is added to convert any formic-acetic anhydride to isopropyl formate. The amount of formic acid used is preferably 1.3 to 1.35 Molar equivalents based on aspartic acid.

Alternatively, the acetic anhydride can be added to the reaction mixture all at once (2.3 –2.9 moles per mole of aspartic acid) at the beginning of the reaction and the secondary alcohol can be added thereafter to consume the excess formic acid by reacting with the mixed anhydride resulting in the formation of the corresponding ester. Also, a minor portion of the acetic anhydride can be added with the secondary alcohol in a single step. Preferably, however, the formic acid, a major amount of the acetic anhydride, and a catalyst are mixed for about 2–3 hours followed by addition of a minor portion of the acetic anhydride. The reaction is then maintained for an additional 2–3 hours with mixing after which the secondary alcohol (isoproponal) is added thereto. This final reaction mixture is then mixed, preferably at about 50° C., for an additional 2–3 hours to completion.

The product, N-formyl-L-aspartic anhydride, is then reacted with L-phenylalanine in situ, thereby doing away with any costly and time-consuming separation techniques. The reaction by-products serve as cosolvents for the coupling process.

L-phenylalanine is coupled with N-formyl-L-aspartic anhydride in equimolar amounts, optionally in the presence of an alkyl ester or a hindered alcohol or a suitable mixture of the two. It has been found that the alkyl ester and/or hindered alcohol increase the $\alpha/\beta$ ratio when added in an amount equivalent to at least about 1.2 moles per mole of L-phenylalanine. The $\alpha/\beta$ ratio increases with increasing amounts of ester or alcohol up to a point where the molar amount of ester, alcohol or combinations thereof is approximately 4.7 times that of L-phenylalanine. At this point, a saturation level is reached wherein the isomer ratio remains constant regardless of how much more ester or alcohol is added.

Preferably, the alkyl ester utilized in the coupling reaction is selected from the group comprising methyl acetate, ethyl acetate, isopropyl acetate, n-butyl acetate and isopropyl formate. Methyl acetate (MeOAc) is a preferred alkyl ester. Hindered alcohols that may be used include isopropyl alcohol and secondary or tertiary butyl alcohol. Isopropyl alcohol is a preferred hindered alcohol. These are the preferred embodiments of the invention and are by no means intended to restrict the use of other alkyl esters or hindered alcohols nor is this intended to limit the scope of this invention.

The coupling reaction is then carried out by stirring the aforementioned mixture for about 4–6 hours at a temperature between about 5°–60° C. and preferably between 15°–30° C., i.e., room temperature. A problem that develops during the coupling reaction is that as the reaction takes place with the formation of N-formyl-L-aspartyl-L-phenylalanine, the mixture or slurry begins to solidify, i.e. high viscosity, to the point where stirring becomes extremely difficult if not impossible. High viscosity to this extent m kes filtration very difficult and inhibits heat transfer which prevents distillation of acetic acid, esters and/or hindered alcohol described below. It has been discovered that by adding acetic acid to the coupling reaction, this solidification is inhibited, i.e a lowering of the viscosity. This is important in that mixing insures completion of the reaction. Moreover, the acid and esters must be removed from the mixture by distillation prior to deformylation. The reaction mixture must be stirrable in order to do this.

The amount of acetic acid added depends upon how much N-formylaspartic anhydride was synthesized. Since the coupling reaction is carried out in situ in the reaction by-products some acetic acid will already be present from the initial reaction between L-aspartic acid and acetic anhydride. The total amount of acetic acid in the system should be about seven (7) times that of L-phenylalanine on a mole/mole basis. Therefore, one would not necessarily add acetic acid in an amount seven times that of the L-phenylalanine that is added. A lesser amount wherein the total molar amount of acetic acid present in the system is about seven times that of the L-phenylalanine is sufficient.

While the coupling reaction can be conducted at ambient temperature, elevated temperatures are preferably employed which also contribute to a lowering of the viscosity of the reaction mixture. Temperatures between 25° C. and 40° C. are advantageously employed, while a preferred temperature is about 30° C.

Another unique aspect of the present invention involves the lowering of the viscosity of the coupling reaction mixture by controlling the agitation of the coupling reaction mixture. It has been discovered that stopping or lowering the speed of the agitator during the coupling reaction dramatically causes a lowering of the viscosity of the coupling reaction mixture. In a large reactor (10 feet diameter reactor fitted with a mechanical stirrer having 5 foot long paddles, very slow agitation, such as 5–40 revolutions per minute (rpm), and occasional agitation, such as, briefly running the agitator every 5–15 minutes, drastically reduce the viscosity of the coupling reaction mixture when compared to reactions conducted with an agitator speed of about 60 or more rpm. In lab scale reactors (4 inch round bottom flask with 3 inch paddles) 200–300 rpm causes a very thick reaction mixture while agitation at 5–15 rpm produces a very pourable low viscosity reaction mixture. Also turning off the agitator after about 1 hour after the L-Phe has been added to the reaction mixture and restarting it after the reaction, i.e., about 6 hours, produces a reaction mixture with a low viscosity. However, in a commercial scale operation where the agitator is stopped for periods over 1 hour it can be very difficult to restart the agitator because of settling and caking of the precipitate. Therefore, slow agitation and periodic agitation are preferred.

When used herein the terms "pourable" or "low viscosity" when referring to the coupling reaction mixtures, mean a liquid which will pour from a glass or reactor vessel. Such liquids generally have a viscosity of under about 15,000 Centipoise (cp), advantageously between 1,000–10,000 cp, and preferably between 150–500 cp.

The means of agitation are not critical in the practice of the present invention. Any standard agitation means can be employed; i.e., injection of an inert gas, shaking, tumbling the reactor, mechanical stirrers, etc. Mechanical stirrers are preferred. The exact stirrer configuration is not critical either. With paddle or blade stirrers, the stirrer speed is advantageously set at from about 5 to about 40 rpm and preferably at about 20 rpm. While the paddle tip speed in meters/second (m/sec) will vary at a set rpm based on the paddle length, it has been found that rpm is more accurate description of the agitator speed in the practice of the present invention. Any stirrer speed under about 40 rpm is acceptable in reducing the viscosity of the reaction mixture. However, it should be noted that in lab scale equipment (4 in. flask) a stirrer speed between 40–150 rpm will produce a pourable reaction mixture.

The alpha and beta isomers of N-formyl-$\alpha$-L-aspartyl-L-phenylalanine ($\alpha/\beta$ F-AP) produced by the above-described invention can be analyzed by high performance liquid chromatography (HPLC) and will show that these processes yield an unusually high $\alpha/\beta$ ratio of approximately 79.5:20.5.

Optionally, acetic acid and any esters (methyl acetate, isopropyl formate, etc.) or hindered alcohol are removed from the reaction mixture prior to the deformylation step described below. Preferably, the acetic acid and esters are vacuum distilled at from about 15 to about 25 inches of mercury. The vacuum distillation is conducted prior to the addition of HCl employed to deformylate the $\alpha/\beta$ F-AP. The acetic acid, esters and/or alcohol are recovered and recycled for use in subsequent coupling reactions.

The alpha and beta isomers of N-formyl-L-aspartyl-L-phenylalanine are then deformylated. Hydrochloric acid, and optionally methanol, are added to the isomer mixture in order to deformylate the $\alpha/\beta$ F-AP resulting in formation of $\alpha/\beta$-AP. Excess methanol also reacts with any left over acetic acid and formic acid present in the reaction mixture to yield methyl acetate and methyl formate which have much lower boiling points than acetic acid or formic acid and thereby can be removed from the system by distillation at lower temperatures.

The resulting mixture of $\alpha/\beta$-AP and their various methyl esters is then esterified by adjusting the concentration of HCl, methanol and water to amounts sufficient to produce a high yield of $\alpha$-APM(HCl). The methanol concentration should be from about 1 to about 10 weight percent and preferably from about 3 to about 5 weight percent. The HCl concentration should be from about 9% to about 18% by weight and preferably from about 12.5% to about 14.5% by weight. The water concentration should be from about 32 to about 50 weight percent and preferably from about 37 to about 42 weight percent. After the concentrations of water, HCl and methanol have been adjusted accordingly, the reaction mixture is gently agitated at temperatures under about 35° C. and preferably at ambient temperature (20°–30° C.). The esterification is complete in about 4 to about 8 days and usually in about 6 days.

The resulting hydrochloride salt of $\alpha$-L-aspartyl-L-phenylalanine methyl ester ($\alpha$-APM(HCl)) is then easily separated from the beta isomer since $\alpha$-APM•HCl•2H$_2$O has a lower solubility in aqueous solutions than $\beta$-APM(HCl). See Ariyoshi sunra. The alpha isomer precipitates from solution and is separated by filtration, centrifugation, decantation or one of many other conventional methods.

The $\alpha$-APM(HCl) is then neutralized with a base to form APM which is then recovered by crystallization techniques well known in the art.

The following examples are provided to specifically demonstrate the invention at hand. These examples are set forth by way of illustration only and it is intended that the invention is not to be construed as being limited either in spirit or in scope by the details contained herein as modifications in both. The materials and methods will be apparent from this disclosure to those skilled in the art.

EXAMPLE 1

0.12 grams (0.003 mole) of magnesium oxide, a catalyst, was dissolved in 16 milliliters (ml) (0.405 mole) of 95% formic acid. 60.2 ml of acetic anhydride was then added to the aforementioned solution which was heated to 35°-40° C. for 10-15 minutes. Subsequently, 39.93 grams (0.3 mole) of L-aspartic acid was added and this mixture was stirred for 2.5 hours at 50±2° C. At this point, an additional 8.6 ml of acetic anhydride was added and the reaction continued for an additional 2.5 hours at 50±2° C. 9.2 ml (0.120 mole) of isopropyl alcohol was then added to the reaction mixture and heating was continued for an additional two hours. N-formyl aspartic anhydride was formed at this point as shown by high performance liquid chromatography (HPLC).

The N-formylaspartic anhydride mixture was then cooled to room temperature, 20°-25° C., and to this was added 150 ml (1.89 moles) of methyl acetate, followed by 44.6 grams (0.27 moles) of L-phenylalanine. The mixture was stirred for 3 hours at room temperature (20°-30° C.). After 3 hours of stirring, the mixture was allowed to stand overnight (18-24 hours) at room temperature and solidified.

The solidified product was dissolved in a solution of methanol and water (9:1). The resulting mixture of alpha and beta isomers of N-formyl-L-aspartyl-L-phenylalanine was analyzed by HPLC and was found to have an $\alpha/\beta$ isomer ratio of 79.2:20.8.

EXAMPLE 2

The $\alpha/\beta$ ratio of N-formyl-L-aspartyl-L-phenylalanine prepared by the in situ coupling reaction was compared using different ester/alcohol cosolvents. Magnesium oxide (0.121 grams; 0.003 mole) was dissolved in 16.4 ml (0.406 mole) of 93.4% formic acid under nitrogen. 62.5 ml (0.655 mole) of acetic anhydride was then added to the stirred mixture forming a white precipitate. The temperature of the mixture rose to 37-38° C. during the course of the next thirty minutes. L-Aspartic acid (39.93 grams; 0.30 mole) was then added and the mixture heated to 48°-50° C. for 2.5 hours. Additional acetic anhydride (8.6 ml., 0.09 mole) was then added with heating for an additional 2.5 hours. 9.2 ml (0.120 mole) of isopropyl alcohol was added to the reaction mixture, heating at 50±2° C. was continued for an additional 2.0 hours. The reaction mixture was then cooled to room temperature (22-27° C.).

The preparation of N-formyl-L-aspartic anhydride was repeated several times in order to prepare multiple first reaction mixtures. To each of these first reaction mixtures was added 100 ml of one of the alkyl ester or hindered alcohol solvents listed in Table 1 followed by the addition of 44.6 grams (0.27 mole) of L-phenylalanine. The resulting slurries were maintained at room temperature for 5 hours for completion of the in situ coupling process. As the reaction proceeded, the slurries became more and more solidified in each reaction and a quantity of a methanol and water solution (10:1) was added in order to dissolve all the solids therein. 2.0 grams aliquots were analyzed in each reaction mixture by HPLC. The resulting $\alpha/\beta$ ratios of N-formyl-L-aspartyl-L-phenylalanine formed in each reaction are as follows:

TABLE 1

| Solvent | $\alpha/\beta$ ratio |
| --- | --- |
| Methyl Acetate | 79:21 |
| Ethyl Acetate | 79:21 |
| Isopropyl Acetate | 80:20 |
| n-Butyl Acetate | 78:22 |
| Methyl Formate | 75.5:24.5 |
| Isopropyl Formate | 78:22 |
| Isopropyl Alcohol | 78:22 |
| sec-Butyl Alcohol | 76:24 |
| tert-Butyl Alcohol | 78:22 |
| No Added Solvent | 71:29 |

EXAMPLE 3

N-Formylaspartic anhydride was again prepared according to the procedure set forth in Example 1. The aspartic anhydride was left in the original reaction mixture to be coupled in situ with L-phenylalanine. 100 ml methyl acetate, 44.6 grams (0.27 mole) L-phenylalanine and 84 ml (1.47 mole) acetic acid were added to the in situ reaction mixture. The total amount of acetic acid present in the reaction mixture equaled 166.4 ml (2.912 moles) since there was some already present as a by-product in the anhydride formation reaction when acetic anhydride reacted with L-aspartic acid.

The coupling reaction mixture was stirred at room temperature (20°-25° C.) for approximately 6 hours. This mixture did not solidify after the coupling reaction was completed. The resulting $\alpha/\beta$ isomer ratio was analyzed using HPLC and was found to be 79.5:20.5.

EXAMPLE 4

N-Formylaspartic anhydride (F-Asp=O) was prepared according to the procedure set forth in Example 1 and was left in the original reaction mixture. The coupling reaction was then carried out in situ whereby 44.6 grams (0.27 mole) L-phenylalanine, 106.89 grams (1.26 moles) methyl acetate and enough acetic acid to provide a total amount of 2.91 moles was added. (See Example 3.)

The coupling reaction was carried out by stirring the mixture for approximately six hours at room temperature (20°-25° C.). This mixture also did not solidify after the coupling reaction was completed. An $\alpha/\beta$ isomer ratio of 79.5:20.5 was achieved.

The following table (Table 3) summarizes the results in terms of $\alpha/\beta$ ratios that were achieved when different concentrations of methyl acetate and acetic acid (HOAc) were introduced into the coupling reaction. The amounts of N-formyl aspartic anhydride and L-phenylalanine were held constant at 0.27 mole for each. Temperature and reaction times were also held constant. The respective concentrations of methyl acetate and acetic acid in each reaction are given in terms of moles of solvent per mole of L-phenylalanine. The respective $\alpha/\beta$ ratios obtained from each mixture are shown to the right to verify the consistency with which a high ratio is obtainable using the present invention.

TABLE 3

$\alpha/\beta$ Ratio vs. HOAc and MeOAc concentration in coupling L—Phe and F—Asp = O

| Experiment # | Concentration moles/moles of L—Phe | | $\alpha:\beta$ Ratio |
| --- | --- | --- | --- |
| | MeOAc | HOAc | |
| 1 | 4.65 | 0.00 | 80.0/20.0 |
| 2 | 4.65 | 5.34 | 78.6/21.4 |

TABLE 3-continued

α/β Ratio vs. HOAc and MeOAc concentration in coupling L—Phe and F—Asp = O

| Experiment # | Concentration moles/moles of L—Phe | | α:β Ratio |
|---|---|---|---|
| | MeOAc | HOAc | |
| 3 | 7.00 | 5.34 | 79.2/20.8 |
| 4 | 4.60 | 10.79 | 79.5/20.5 |
| 5 | 3.49 | 10.79 | 79.2/20.8 |
| 6 | 2.33 | 10.79 | 77.9/22.1 |
| 7 | 1.17 | 10.79 | 77.1/22.9 |
| 8 | 2.94 | 9.00 | 77.4/22.6 |
| 9 | 3.50 | 9.00 | 78.0/22.0 |
| 10 | 2.28 | 7.00 | 77.15/22.85 |
| 11 | 1.17 | 8.58 | 76.3/23.7 |
| 12 | 2.61 | 7.67 | 77.8/22.2 |
| 13 | 0.00 | 5.34 | 69.0/31.0 |
| 14 | 0.00 | 10.50 | 74.0/26.0 |

EXAMPLE 5

Although it is advisable that the amount of acetic acid in the coupling reaction is generally seven times that of L-phenylalanine, it was demonstrated that even a small amount will act as a catalyst. N-formylaspartic-anhydride (31.0 grams; 0.217 mole), prepared according to the process set forth in Example 2, was mixed with 150 ml of methyl acetate and 25.8 ml (0.45 mole) of acetic acid under nitrogen. 33.0 grams (0.20 mole) of L-phenylalanine was then added and the mixture stirred at approximately 25° C. After 3.5 hours, an additional 100 ml of methyl acetate was added to prevent solidification and this was repeated after 4.5 hours. After a total of 6 hours, the reaction slurry was dissolved in a sufficient amount of methanol and water (10:1). The solution was assayed by HPLC and the α/β isomer ratio was determined to be 80:20.

EXAMPLE 6

Magnesium oxide (0.4 grams; 0.01 moles) was dissolved in 53.3 ml (1.35 moles) of 95% formic acid and 200 ml (2.10 moles) acetic anhydride. The reaction therein generated an increase in temperature to 40° C. (from 20°-22° C.) over a period of 15 minutes. L-aspartic acid (133.1 grams; 1.0 mole) was added to the reaction mixture and the resulting slurry was heated at 48°-50° C. for 2.5 hours at which point 28.9 ml (0.303 mole) of additional acetic anhydride was added. Heating was continued for another 2.5 hours after which 30.7 ml (0.4 mole) of isopropyl alcohol was mixed in. This mixture was stirred for 1.5 hours at 48°-50° C. and then permitted to cool to room temperature (25°±2° C.). The resulting mixture contained N-formylaspartic anhydride.

To this reaction mixture was added 187 ml methyl acetate and 148.68 g (0.9 mole) of L-phenylalanine yielding a slurry that was stirred for 1.5 hours. 120 ml of acetic acid was added to facilitate stirring and the mixture was maintained at 25°-26° C. for an additional 4.5 hours. The mixture was then distilled under vacuum (22 in. mercury), until the reaction mixture reached a temperature of 65° C.

Methanol (220 ml) and 100 ml hydrochloric acid (1.2 moles) were mixed into the slurry which was heated to approximately 60° C. for 1 hour. A clear solution was obtained which was distilled until a head temperature of 63° C. and a reaction mixture temperature of 73° C. was reached. Additional methanol (400 ml) was added and distillation continued until a reaction mixture temperature of 85° C. was reached. The resulting residue was cooled to room temperature (approx. 25° C.) by subjecting the reaction mixture to a vacuum of approximately 26 inches mercury for 45 min. To the cooled residue was then added 120 ml 37% hydrochloric acid, 19 ml methanol and 94.8 ml water. The mixture was then stirred at room temperature for six days.

The resulting slurry was filtered and washed to yield a white solid (197.54 g.) after drying at 50° C. for 10 hours. This material was assayed by HPLC to reveal that the product contained 61.5% α-APM.

EXAMPLE 7

The same procedure as Example 6 was followed except that the 400 ml of methanol was added at a rate sufficient to maintain a constant volume. The resulting solid (197.85 g) was assayed by HPLC which indicated an α-APM content of 67.18%.

EXAMPLE 8

The same procedure as Example 7 was followed except that the final distillation was conducted entirely under vacuum at a maximum pot temperature of 55°-56° C. The yield of L-aspartyl-L-phenylalanine methyl ester as the hydrochloride salt was 51% of theoretical.

EXAMPLE 9

The same procedure as Example 7 was followed except that the distillation after methanol addition was conducted under vacuum (20 in mercury) for 2 hours at 55°-67° C. A yield of 186.15 g of α-L-aspartyl-L-phenylalanine methyl ester hydrochloride dihydrate was isolated and assayed, revealing that 64.68% was α-L-aspartyl-L-phenylalanine methyl ester.

EXAMPLE 10

Formic acid (95.7%, 16 ml 0.405 mole) was added dropwise to 60.2 ml (0.631 mole) of acetic anhydride over 5 min/during which time the temperature rose to 40° C. The mixture was stirred for 55 min and 0.43 g (0.003 moles) of magnesium acetate and 39.93 g (0.3 mole) of L-aspartic acid were added. The resulting slurry was heated at 47°-48° C. for 2.5 hr. Acetic anhydride (7.1 ml; 0.0744 mole) was added and the heating was continued for 2.5 hr. Isopropyl alcohol (7.21 g; 0.120 mole) was added and the heating was continued for 1.5 hr. Heating was discontinued and 130 mls. of acetic acid and 44.6 g (0.270 mole) of L-phenylalanine was added. This mixture was stirred at ambient temperature overnight. The resulting slurry was dissolved in 750 ml of water and 1.05 liters of methanol and weighed. An aliquot was withdrawn and assayed for α/β-N-formyl-L-aspartyl-L-phenylalanine by HPLC. The yield of the α-isomer was determined to be 71.5%.

EXAMPLE 11

Formic acid (16.0 mls., 0.405 moles) was added to 0.121 g (0.003 mole) of magnesium oxide under nitrogen and stirred until all the solid was dissolved. Acetic anhydride (60.2 ml;, 0.631 mole) was added, giving a precipitate immediately and a temperature increase to 40° C. over 15 min. L-aspartic acid (39.93 g; 0.3 mole) was added and the slurry heated to 48°-50° C. for 2.5 hr. Additional acetic anhydride (9.3 ml; 0.0974 mole) was added and heating continued for 2.5 hr Isopropyl alcohol (11.9 ml; 0.155 mole) was added and the mixture heated for 1.5 hr. The temperature was increased to 53° C. and 44.6 g (0.27 mole) of L-phenylalanine was added in four portions over 15 min. The temperature rose to 58° C. in 10 min and stirring was continued for 50 min longer. This reaction mixture was then allowed to cool to ambient temperature. 30.1 ml of 37% hydrochloric acid and 70 ml of water were added. The slurry was heated to 60° C. and held there for 1 hr. during which time all the solid dissolved. The solvent was removed by distilling under vacuum at a pot temperature of 55±2° C. The residue weighed 119 g. To the residue was added 100 g of water and distillation was repeated to yield a residue weight of 107 g. 50.5 ml hydrochloric acid, 41.2 ml water and 31.5 ml methanol were added and the slurry allowed to stir at 20°-30° C. for 4 days. The solid was filtered and washed with 50 ml of saturated brine. The white, crystalline α-L-aspartyl-L-phenylalanine methyl ester hydrochloride dihydrate weighed 43.95 g after drying overnight.

EXAMPLE 12

A suspension of N-formylaspartic anhydride was prepared as in Example 1. Methyl acetate (75 ml) and 84 ml of acetic acid were added prior to the addition of L-phenylalanine (44.6 g) and the resulting slurry was stirred for 6 hr at 20°-30° C. Solvent (350 g) was removed by distillation under 50mm/Hg vacuum. Hydrochloric acid (37%; 30 ml) and 66.7 ml methanol were added and heated at 60°-62° C. for 1 hr. Additional methanol (528 ml) was added and distilled to a pot temperature of 85° C. A 26 in vacuum was applied and the solvent distilled to a pot temperature of 30° C. 36.4 ml hydrochloric acid, 24.4 ml water, and 5.5 ml methanol then were added and the resulting mixture stirred for 4 days. The resulting precipitate was filtered, washed and dried to yield 63.1 g of white solid. HPLC assay showed an α-APM content of 63%.

EXAMPLE 13

Various suspensions of N-formyl-L-aspartic anhydride (F-Asp=O) were prepared as in Example 1 and placed in a 500 ml round bottom flask equipped with a Talboys model 134-2 mechanical stirrer. Methyl acetate (MeOAc), acetic acid (HOAc) and L-phenylalanine (Phe) were added to these reaction mixtures in amounts wherein the mole ratio of MeOAc/HOAc(total)/Phe/F-Asp=O was 2.73/10.64/1.0/1.0. These reaction mixtures were run at room temperature for 1 hour at an agitator speed of 200-300 rpm. At the 1 hour point, the temperature was increased to 40° C. and the agitator rotation was reduced to between 5-15 rpm. Substantially complete conversion of Phe occurred in 3 hours. A Brookfield viscometer LV was used to measure viscosities at room temperature after a 6 hour reaction period including 1.5-2.0 hours reaction finishing at 50°-55° C. The results are given below:

| Agitator Speed After 1st Hr | Temperature After 1st Hr | Viscosity in cP (RPM-Spindle 2) | | | |
|---|---|---|---|---|---|
| | | 6* | 12* | 30* | 60* |
| 200-300 rpm (control) | room | 2860 cP | 1587 cP | 819 cP | 483 cP |
| 5-15 rpm | 25° C. | 1225 | 937 | 490 | 301 |
| 5-15 rpm | 40° C. | 690 | 485 | 287 | 170 |

*rpm of spindle

EXAMPLE 14

Substantially the same procedures described in Example 13 were conducted with the exception that the reaction mixture was not stirred at all after the 1st hour of the reaction. After a total of 6 hours the reaction mixture could be stirred, however, assistance was required to start the stirrer. Once started, the reaction mixture was very fluid and pourable and was much less viscous than a reaction mixture stirred at 200-300 rpm for the whole 6 hours. Analysis of the reaction mixture revealed complete Phe conversion.

EXAMPLE 15

Substantially the same procedures of Example 13 were conducted with the exception that the reaction mixture was stirred briefly, i.e., for 12 seconds at low speed, every 5-15 minutes after the 45 minutes of the reaction. For the first hour the reaction mixture was stirred at 200-300 rpm. The reaction mixture was a pourable liquid at the end of the reaction. Analysis of the reaction mixture revealed complete Phe conversion.

EXAMPLE 16

A suspension of N-formyl-L-aspartic anhydride (F-Asp=0) was prepared as in Example 1 and placed in a 500 ml round bottom flask equipped with a Talboys model 134-2 mechanical stirrer. MeOAc, HOAc and Phe were added to the reaction mixture in amounts wherein the mole ratio of MeOAc/HOAc(total)/Phe/F-Asp=0 was 2.73/7.84/1.0/1.0. The reaction mixture was run at room temperature for 1 hour at an agitator speed of 200-300 rpm. At the end of 1 hour the agitator speed was reduced to 5-15 rpm. Complete conversion of Phe was accomplished in about 5 hours. Two controls were also run where the agitator speed was 200-300 rpm for 6 hours. A Brookfield viscometer LV was used to measure the viscosities at room temperature after a 6 hour reaction period including a 1.5-2 hr. reaction finishing at 50°-55° C. The results are given below:

| Agitator Speed After 1st Hr. | Viscosity in cP (RPM-Spindle 4) | | |
|---|---|---|---|
| | 12* | 30* | 60* |
| 200-300 rpm (control) | 9,100 cP | 6,740 cP | 5,110 cP |
| 200-300 rpm (control) | 12,000 | 8,000 | 6,000 |
| 5-15 rpm | 6,850 | 3,740 | 2,410 |

*rpm of spindle

EXAMPLE 17

Substantially the same procedures described in Example 16 were conducted with the exception that the temperature of the reaction mixture was elevated to 40° C. when the agitator speed was reduced to 5-15 rpm. The resulting reaction mixture was very pourable and much less viscous than the controls run at 200-300 rpm. Analysis indicated total Phe conversion.

In similar operations α-APM(HCl) was produced in a good yield while employing the various alkyl esters, hindered alcohols, agitation parameters and distillation techniques described herein.

What is claimed is:

1. A method of preparing α/β-N-formyl-L-aspartyl-L-phenylalanine isomers which comprises:
   (a) reacting N-formyl-L-aspartic anhydride with L-phenylalanine,
   (b) in the presence of acetic acid and an alkyl ester or a hindered alcohol, and
   (c) under agitation conditions sufficient to form a final reaction mixture which is pourable.

2. The method of claim 1 wherein the agitation is achieved with a mechanical stirrer at a speed less than about 40 revolutions per minute (rpm).

3. The method of claim 2 wherein the speed of the stirrer is about 20 rpm.

4. The method of claim 1 wherein the reaction mixture is agitated periodically throughout the reaction.

5. The method of claim 2 wherein the reaction is conducted at a temperature under about 60° C.

6. The method of claim 5 wherein the temperature is about 30° C.

* * * * *